United States Patent [19]
Gao et al.

[11] Patent Number: 5,545,745
[45] Date of Patent: Aug. 13, 1996

[54] ENANTIOSELECTIVE PREPARATION OF OPTICALLY PURE ALBUTEROL

[75] Inventors: Yun Gao, Southborough; Charles M. Zepp, Hardwick, both of Mass.

[73] Assignee: Sepracor, Inc., Marlborough, Mass.

[21] Appl. No.: 376,072

[22] Filed: Jan. 20, 1995

Related U.S. Application Data

[63] Continuation-in-part of Ser. No. 247,302, May 23, 1994, Pat. No. 5,399,765.

[51] Int. Cl.⁶ .................................................. C07C 209/68
[52] U.S. Cl. ........................... 560/42; 564/304; 564/356; 564/363; 564/365
[58] Field of Search ............................. 560/42; 564/304, 564/356, 363, 365

[56] References Cited

FOREIGN PATENT DOCUMENTS

WO92/04314  3/1992  WIPO .

OTHER PUBLICATIONS

Hartley et al. "Absolute Configuration of the Optical Isomers of Salbutamol" *J. Med. Chem.* 14, 895–896 (1971).
Hopkins, "Salbutamol" *Drugs of the Future IV* 629–633 (1979).
Floyd et al. "The Oxidation of Aetophenones to Arylglyoxals with Aqueous Hydrobromic Acid in Dimethyl Sulfoxide" *J. Org. Chem.* 50 5022–5027 (1985).
Collin et al. "Saligenin Analogs of Sympathomimetic Catecholamines" Chemistry Dept., Allen and Hansburys Ltd. (1970).

*Primary Examiner*—Richard L. Raymond
*Attorney, Agent, or Firm*—Heslin & Rothenberg, P.C.

[57] ABSTRACT

The invention relates to a method for producing albuterol by the resolution of a mixture of enantiomers of methyl 5-[2-[(1,1-dimethylethyl)amino]-1-hydroxyethyl]-2-(phenylmethoxy)benzoate or α-[[(1,1-dimethylethyl)amino]methyl]-4-(phenylmethoxy)-1,3-benzenedimethanol using a chiral acid such as (+/−) di-toluoyltartaric acid or (+/−) di-benzoyltartaric acid.

17 Claims, No Drawings

ENANTIOSELECTIVE PREPARATION OF OPTICALLY PURE ALBUTEROL

CROSS-REFERENCE TO RELATED APPLICATION

This application is a continuation-in-part of application Ser. No. 08/247,302, filed May 23, 1994, now U.S. Pat. No. 5,399,765.

TECHNICAL FIELD

The present invention relates to a method of preparing optically pure (R) and (S) albuterol. More particularly, the present invention relates to the preparation and resolution of the albuterol precursor methyl 5-[2-[(1,1-dimethylethyl)amino]-1-hydroxyethyl]-2-(phenylmethoxy) benzoate or α-[[(1,1-dimethylethyl)amino]methyl]-4-(phenylmethoxy)-1,3-benzenedimethanol with a chiral acid.

BACKGROUND OF THE INVENTION

Albuterol, also referred to as α-[[(1,1-dimethylethyl)amino]methyl]-4-hydroxy-1,3-benzenedimethanol or as salbutamol, is a β-2 agonist useful as a bronchodilator. It possesses a high degree of selectivity between β-1 receptors (which are present in the heart) and β-2 receptors (which are present in bronchial tissue and elsewhere), for which reason it is widely used in the treatment of asthma, since in therapeutic doses it exhibits fewer cardiac side effects than many other β-agonists.

It is known that among many drugs having chiral centers one enantiomer of a racemic pair is often more active than the other in treating a medical condition. Recent data suggest that the levorotatory R-isomer of albuterol is approximately 80 times more potent than the dextrorotatory S-isomer (Hartley and Middlemis, *J. Med. Chem.* 14 895–896 (1971)), and preliminary research indicates that administration of the pure R-enantiomer may offer an improved therapeutic ratio.

Methods of producing optically pure albuterol by resolving methyl benzoate albuterol precursors are described only for precursors having the amine protected by a benzyl group. Hartley et al. op. cit. teaches optical resolutions only when both the phenolic group and the amine of the precursor were protected with a benzyl group. The process described by Hartley required the use of expensive starting materials, involved at least 6 independent steps and produced low overall yields. Therefore, there exists a need for a more economical and efficient method of making optically pure albuterol.

SUMMARY OF THE INVENTION

It is an object of the invention to provide a method for obtaining an optically pure isomer of albuterol from a mono-protected albuterol precursor.

It is a further object to provide a manipulatively simple synthesis of optically pure albuterol from a commercially available prochiral starting material in only four steps involving one highly efficient resolution.

This and other objects, features and advantages are provided by the present invention which relates in one aspect to a process for obtaining a single enantiomer of albuterol, comprising:

dissolving a mixture of enantiomers of methyl 5-[2-[(1,1-dimethylethyl)amino]-1-hydroxyethyl]-2-(phenylmethoxy)benzoate and a chiral acid in methanol, ethanol or a mixture of the two by heating to form a solution, said chiral acid being selected from the group consisting of (−)-di-toluoyl-L-tartaric acid, (+)-di-toluoyl-D-tartaric acid, (−)-di-benzoyl-L-tartaric acid and (+)-di-benzoyl-D-tartaric acid;

allowing said solution to cool, whereby a salt of primarily one enantiomer crystallizes;

separating said salt from said solution;

liberating the enantiomer from said salt by treatment with a base;

reducing said enantiomer;

debenzylating said enantiomer and recovering a single enantiomer of albuterol.

In a further aspect, the invention may be characterized as a process for making optically pure albuterol, comprising:

dissolving a mixture of enantiomers of α-[[(1,1-dimethylethyl)amino]methyl]-4-(phenylmethoxy)-1,3-benzenedimethanol and a chiral acid in methanol, ethanol or a mixture of the two by heating to form a solution, said chiral acid being selected from the group consisting of (−)-di-toluoyl-L-tartaric acid, (+)-di-toluoyl-D-tartaric acid, (−)-di-benzoyl-L-tartaric acid and (+)-dibenzoyl-D-tartaric acid;

allowing said solution to cool, whereby a salt of primarily one enantiomer crystallizes;

separating said salt from said solution;

liberating said single enantiomer from said salt by treatment with a base;

debenzylating said enantiomer and recovering optically pure albuterol.

In either process described above, a chiral acid such as (−)-di-toluoyl-L-tartaric acid or (−)-di-benzoyl-L-tartaric acid will give the S enantiomer of albuterol; (+)-di-toluoyl-D-tartaric acid or (+)-di-benzoyl-D-tartaric acid will give the R enantiomer of albuterol.

DETAILED DESCRIPTION

The present invention relates to a more economical and efficient process for making optically pure albuterol. The method is particularly economical and efficient because it proceeds via readily available and inexpensive starting materials, as set forth in Scheme A below:

Scheme B

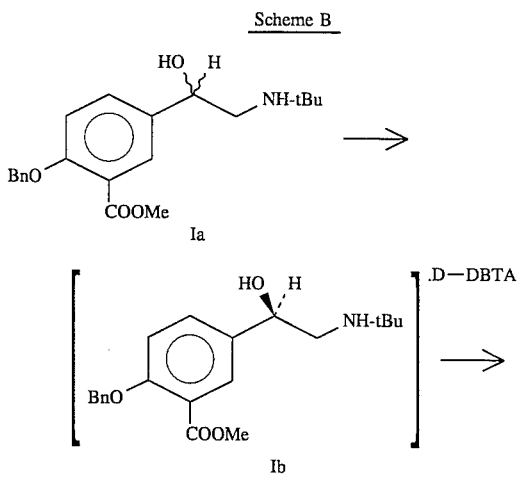

-continued
Scheme B

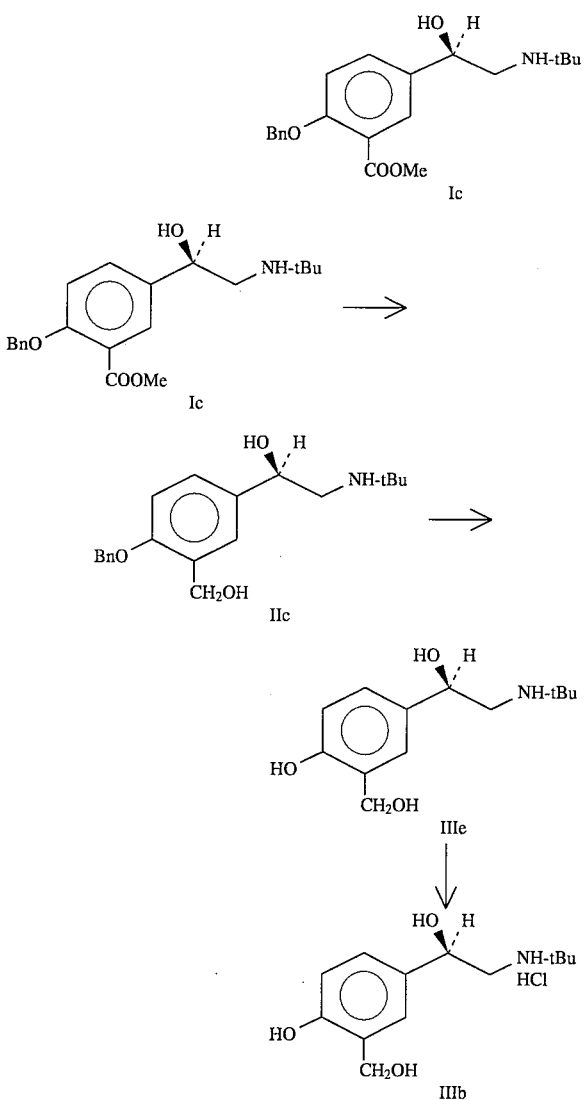

The graphic representations of racemic, ambiscalemic and scalemic or enantiomerically pure compounds used herein are taken from Mayer *J. Chem. Ed.* 62, 114–120 (1985). Thus, solid and broken wedges are used to denote the absolute configuration of a chiral element; wedge outlines and dotted or broken lines denote enantiomerically pure compounds of unspecified absolute configuration (e.g. structures Ib and IIIb). As usual, a wavy line indicates a mixture of enantiomers of indeterminate proportion, commonly a racemic mixture.

Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. There is no correlation between nomenclature for the absolute stereochemistry and for the rotation of an enantiomer. Thus, D-lactic acid is the same as (−) lactic acid, and L-lactic acid is (+). Compounds having a single chiral center exist as a pair of enantiomers which are identical except that they are non-superimposable mirror images of one another. A one-to-one mixture of enantiomers is often referred to as a racemic mixture.

The term "enantiomeric excess" is well known in the art and is defined for a resolution of ab→a+b as $$ee_a = \left( \frac{\text{conc. of } a - \text{conc. of } b}{\text{conc. of } a + \text{conc. of } b} \right) \times 100$$

The term "enantiomeric excess" is related to the older term "optical purity" in that both are measures of the same phenomenon. The value of ee will be a number from 0 to 100, 0 being racemic and 100 being pure, single enantiomer. A compound which in the past might have been called 98% optically pure is now more precisely described as 96% ee. Processes that yield products of ee less than about 80% are not generally regarded as commercially attractive. Processes that yield albuterol of ee greater than about 96% are particularly attractive because the eutectic of albuterol is about 96–97% and thus substantially pure single enantiomers can be obtained by simple recrystallization of the product. "Optically pure" and "substantially optically pure" as used herein refer to albuterol of 96% ee or greater.

5-[2-[(1,1-dimethylethyl)amino]-1-hydroxyethyl]-2-(phenylmethoxy)-benzoate (structure Ia and hereinafter "compound Ia") may be prepared by procedures well known to persons skilled in the art. The starting material shown in Scheme A above, compound Ia, is commercially available from Cipla (Bombay, India).

Without further purification compound Ia is resolved with a chiral acid such as (−) or (+) di-p-toluoyltartaric acid or (−) or (+) di-benzoyltartaric acid. This may be accomplished by dissolving compound Ia and the chiral acid in refluxing methanol. The solvent may alternatively comprise ethanol or a methanol/ethanol mixture. Resolution of compound Ia may be accomplished with either about 1 mole equivalent of the tartaric acid derivative or with about 0.5 mole equivalent of the chiral acid (structure Ib and hereinafter "compound Ib salt") in the form of a solid. Compound Ib salt is filtered off, washed with ethyl acetate to remove impurities and then dried.

TABLE 1

| | Resolution of racemic compound Ia | | | |
|---|---|---|---|---|
| Scale of compound Ia | Conditions | Yield of compound Ib | Chem. purity | ee |
| 3 mmol | 1.0 eq of D-TA | 31.6% | N.D. | 10.0% |
| 10 mmol | 0.5 eq of (D)-TA | 23.0% | N.D. | 10.6% |
| 200 mmol | 0.5 eq. of D-DBTA | 28.7% | 99.9% area | 99.3% |

TABLE 1-continued

Resolution of racemic compound Ia

| Scale of compound Ia | Conditions | Yield of compound Ib | Chem. purity | ee |
|---|---|---|---|---|
| 100 mmol | 0.5 eq of D-DBTA | 37.2% | 99.9% area | 99.0% |
| 3 mmol | 1.0 eq of D-DTTA | 37.2% | N.D. | 84.3% |

The solid, compound Ib salt, is preferably dissolved again in refluxing methanol and the resulting solution cooled to room temperature and stored at 0° to 5° C. for 10 to 20 hours. The solid is again collected by means known in the art, such as by filtration, and dried to produce a diastereomeric salt of approximately 99.0% ee, from which optically active (S) or (R) methyl 5-[2-[(1,1-dimethyl ethyl)amino]-1-hydroxy-ethyl-2-(phenylmethoxy)benzoate (structure Ic and hereinafter "compound Ic") may be obtained by treatment with base and, if desired, recrystallization from ethyl acetate.

Compound Ic is reduced to substantially optically pure α-[[(1,1-dimethylethyl)amino]methyl]-4-(phenylmethoxy)-1,3-benzenedimethanol (structure IIc and hereinafter "4-benzyl albuterol"), by treatment with 2 to 3 equivalents of borane-THF solution ($BH_3$-THF) in a suitable solvent, such as tetrahydrofuran (THF). The solution may be refluxed and then cooled and quenched with methanol. In addition, these steps are preferably performed under anhydrous conditions, such as a dry nitrogen or argon atmosphere, and the reactants and products protected from light. The reaction is quenched with methanol and then worked up as usual in the art.

TABLE 2

Reduction of resolved compound Ic

| Scale of compound Ic | Reagent | Isolated yield of compound IIc | Chem. purity | ee |
|---|---|---|---|---|
| 33.3 mmol | $BH_3$-THF | 73.8% | 99.8% | 99.4% |
| 33.3 mmol | $BH_3$-THF | 54.7% | 97.7% | 99.8% |

The optically pure 4-benzyl albuterol (structure IIc), may then be debenzylated to provide optically pure albuterol (structure IIIa). For example, 4-benzyl albuterol may undergo debenzylation with hydrogen in the presence of a catalytic amount of Pd/C in methanol or ethanol at ambient temperature under 50 psi of hydrogen for several hours. After debenzylation the catalyst may be removed by filtration. Optically pure albuterol (structure IIIa) may then be further purified and readily obtained from the filtrate as an acid salt (structure IIIb) by treating the albuterol with an appropriate acid, such as anhydrous HCl, in an ethanol and ether solution.

TABLE 3

Debenzylation and hydrochloride salt formation

| Scale of (ee %) | Yield of (R)-albuterol HCl (%)[a] (g) | Chem. purity (%) | ee (%) |
|---|---|---|---|
| 20.0 mmol (99.4) | 83.5 (4.60) | 99.3 | 99.6 |
| 15.0 mmol (99.8) | 80.4 (3.33) | 99.4 | 99.8 |

[a]Yield after recrystallization.

The highly efficient synthesis shown in Scheme A is made possible by the surprising discovery that the mono-protected ether of compound Ia can be resolved in good yield in a single recrystallization employing a relatively inexpensive chiral acid. Previous syntheses required either more expensive starting materials or additional protection and deprotection steps.

In an alternative embodiment, optically pure albuterol may be economically and efficiently made by similarly starting with inexpensive starting materials and proceeding via a process that further minimizes the requisite steps. This alternative embodiment may be seen in reference to Scheme B as set forth below:

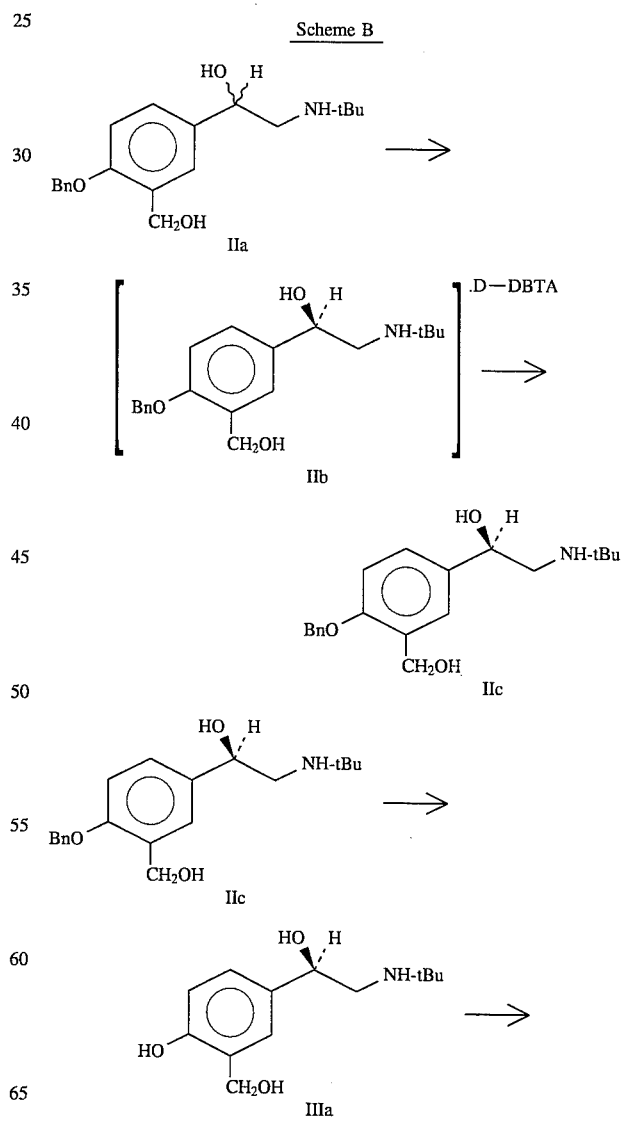

Scheme B (continued)

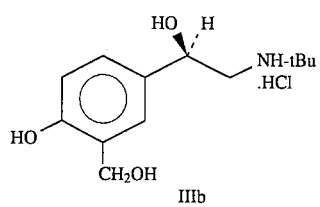
IIIb

The alternative embodiment begins with a mixture of enantiomers of α-1[[(1,1-dimethylethyl)amino]methyl]-4-(phenylmethoxy)-1,3-benzenedimethanol (structure IIa and hereinafter "4-benzyl albuterol"). As with the compound Ia above, racemic 4-benzyl albuterol (IIa) is commercially available from Cipla (Bombay, India). Alternatively, compound IIa (racemic 4-benzyl albuterol) can be prepared by reduction of racemic Ia with borane or LiAlH$_4$. Racemic 4-benzyl albuterol, as well as non one-to-one mixtures of enantiomers, may be resolved using about 1 equivalent of a chiral acid such as (−) or (+) di-p-toluoyltartaric acid (DTTA) or (−) or (+) dibenzoyltartaric acid (DBTA). The solvent may comprise ethanol or ethyl acetate, although ethanol is a preferred solvent when using dibenzoyltartaric acid as the resolving agent. The resolved chiral acid salt (structure IIb) is isolated as a solid and is treated with a base, such as 5 wt % aqueous Na$_2$CO$_3$ in the presence of ethyl acetate in order to obtain the resolved free base of 4-benzyl albuterol (structure IIc). The resolved free base of 4-benzyl albuterol may be further purified by crystallization from ethyl acetate and heptanes in order to achieve 99.8% chemical purity and a ≧98% ee.

TABLE 4

Resolution of racemic benzyl albuterol:

| Entry | Scale of compound IIa | Conditions | Yield[a] of compound IIb | ee |
|---|---|---|---|---|
| 1 | 30.0 mmol | 1 eq of D-DBTA ethanol[b] | 32.5% | 98.4% |
| 2 | 90.0 mmol | 1 eq of D-DBTA | 34.0% | 99.6% |
| 3 | 2 mmol | 1 eq of D-DBTA[c] | 21.7% | 94.4% |
| 4 | 2 mmol | 1 eg of D-DBTA | 50.0% | 83.5% |
| 5 | 2 mmol | 1 eq of D-DTTA ethyl acetate | 46.0% | 75.9% |

[a]Yield is based upon racemic 4-benzyl albuterol compound.
[b]Denatured ethanol.
[c]95% ethanol.

The free base of optically pure 4-benzyl albuterol (IIc) may then be debenzylated to form optically pure albuterol (IIIa) and recrystallized in the form of an acid salt (structure IIIb) as described above in reference to scheme A.

TABLE 5

Debenzylation of compound IIc and hydrochloride salt formation

| Entry | Scale (ee %) | Yield of (R)-albuterol HCl (%) (g) | Chem. purity (%) | ee (%) |
|---|---|---|---|---|
| 1 | 9.7 mmol (98.4) | 80.9 (2.17) | 99.6 | 99.6 |
| 2 | 10.0 mmol (99.6) | 78.3 (2.16) | 99.6 | 99.4 |
| 3 | 10.0 mmol (99.6) | 80.5 (2.22) | 99.4 | 99.8 |

EXAMPLE-1

Racemic compound Ia (1.07 g, 3 mmol) and (+)-D-di-p-toluoyltartaric acid (D-DTTA) (1.21 g, 3 mmol) are dissolved in 36 mL of methanol and refluxed for 10 min. The resulting solution is then cooled to room temperature and stirred for about 4 hours. The white solid formed is isolated by filtration and dried under vacuum to give (R)-compound Ib, the chiral acid salt of compound Ia (0.83 g, 37.2% yield). The salt is neutralized with 5 wt % aq. Na$_2$CO$_3$ and extracted with ethyl acetate to give optically active (R) form of compound Ic, the free base of compound Ib, as a white solid with 84.3% ee. The optical purity (ee) is determined by chiral HPLC (Column Sumichiral OA 4900, 5μ, 4.6×250 mm column; Mobile phase: 240 (hexane): 140 (dichloromethane): 20 (methanol): 1 (trifluoroacetic acid) (vol); UV detection: 280 nm).

EXAMPLE-2

(+)-D-dibenzoyltartaric acid (D-DBTA) (17.9 g, 50 mmol, 0.5 eq) is dissolved in 200 mL of methanol with heating to reflux. A solution of racemic compound Ia (35.7 g, 100 mmol, 1.0 eq) in 200 mL of methanol is added to the above solution over 5–10 min. After addition, a white slurry is formed rapidly which is refluxed for 2 hours. The white slurry is then cooled to room temperature and stirred overnight. The solid is collected by filtration and dried under vacuum (20% ee). The solid is then re-slurried in 600 mL of methanol under reflux for 2 hours and cooled to room temperature and stirred for 4 hours. The solids are collected by filtration and dried under vacuum at room temperature for 2 hours to give a chiral acid salt, the (R) form of compound Ib (23.8 g, 94.8% ee). The salt (21.5 g, 40.1 mmol) is then treated with 100 g of 5 wt % aq. Na$_2$CO$_3$ in 300 mL of ethyl acetate. After phase separation, the ethyl acetate phase is washed with 50 mL each of saturated aq. NaHCO$_3$ and NaCl solutions and concentrated to dryness to give the free base of compound Ib, (R) form of compound Ia, as a white solid. The crude free base is then recrystallized from 15 mL of methanol and 30 mL of ethyl acetate to give purified (R) form of compound Ic as a white solid (12.0 g, 37.2% yield from racemic compound Ia, 99.0% ee and 99.9% purity).

EXAMPLE-3

BH$_3$-THF solution (1.0M in THF, 100 mL, 3.0 eq) is added dropwise over 30 minutes to a mixture of the (R) form of compound Ic taken from Example-2 (12.0 g, 33.3 mmol, 1.0 eq) and 50 mL THF at room temperature under nitrogen atmosphere. The resulting solution is refluxed for 23 hours and cooled and quenched with 30 mL of methanol. The solution is concentrated to ca. 20 mL in volume and diluted with 250 mL of ethyl acetate. The solution is stirred with 40 mL of 5 wt % aq. Na$_2$CO$_3$ at room temperature for 30 minutes. After removal of the aqueous layer, the organic phase is washed with 40 mL each of saturated aq. NaHCO$_3$ and NaCl solution and concentrated to dryness to give a crude (R)-4-benzyl albuterol (compound IIc) as an oily foam. The crude 4-benzyl albuterol is then recrystallized from 20 mL of ethyl acetate and 20 mL of n-heptane to give pure (R)-4-benzyl albuterol as white solid (8.1 g, 73.8% yield, 99.4% ee, 99.8% purity).

EXAMPLE-4

A mixture of (R)-4-benzyl albuterol from Example-3 (6.6 g, 20 mmol) and 10% Pd/C (1.32 g) in 50 mL of ethanol (denatured with 5 vol % 2-propanol) is shaken on a Parr-hydrogenator under 50 psi of hydrogen at room temperature for 2–3 hours. The catalyst is removed by filtration and the filtrate is concentrated to give crude (R)-albuterol (compound IIIa). The crude albuterol (20 mmol) is dissolved in 20 mL of ethanol and treated with anhydrous HCl in ether (1.0M, 19 mL, 0.95 eq) at 0°–5° C. After 30 min at room temperature, 20 mL of methyl t-butyl ether (MTBE) is added to the mixture and the resulting mixture is stirred at room temperature for 30 min and at 0°–5° C. for 2 hours. The white solid (R)-albuterol hydrochloride (compound IIIb) is collected by filtration and recrystallized from 52 mL of ethanol and 26 mL of MTBE to give pure (R)-albuterol hydrochloride as a white powder (4.6 g, 83.5% yield, 99.6% ee, 99.3% purity).

EXAMPLE-5

Racemic 4-benzyl albuterol (compound IIA) (0.66 g, 2 mmol) and D-DTTA (0.81 g, 2 mmol) are dissolved in 5 mL of ethyl acetate with heating. The solution is then cooled to room temperature and stirred for 4 hours. The resulting white solid is collected by filtration and dried under vacuum to give the (R) form of the chiral acid salt, compound IIb (0.66 g, 46% yield, 75.9% ee). The optical purity (ee) is determined on the free base by HPLC as in Example-1.

EXAMPLE-6

Racemic 4-benzyl albuterol (compound IIa) (0.66 g, 2 mmol) and (D-DBTA) (0.72 g, 2 mmol) are dissolved in 4 mL of ethyl acetate with heating at reflux for 10 min. The solution is then cooled to room temperature and stirred for 3 hours. The resulting solid is collected by filtration and dried to give (R) form of the chiral acid salt, compound IIb (0.07 g, 50% yield, 83.5% ee).

EXAMPLE-7

Racemic 4-benzyl albuterol (compound IIa) (0.66 g, 2 mmol) and D-DBTA (0.72 g, 2 mmol) are dissolved in 3.3 mL of 95% ethanol. The solution is heated at reflux for 10 min. and cooled to room temperature and stirred for 7 hours after seeding. The resulting solid is collected by filtration and dried to give the (R) form of the chiral acid salt, compound IIb (0.30 g, 21.7% yield, 94.4% ee).

EXAMPLE 8

D-DBTA (32.2 g, 90 mmol, 1.0 eq) is added to a hot solution of racemic 4-benzyl albuterol (compound IIa) (29.6 g, 90 mmol, 1.0 eq) in 180 mL of anhydrous denatured ethanol (type 3A, denatured with 5 vol % 2-propanol). The resulting solution is refluxed for 15 min. and cooled to room temperature over 40 min and seeded with 99% ee (R)-4-benzyl albuterol D-DBTA salt (compound IIb). The mixture is cooled to 5°–10° C. and stirred for 1 hour. The white solid is collected by filtration and dried at 40° C. and 28 inches of Hg for 1 hour to give (R)-4-benzyl albuterol D-DBTA salt (compound IIb) (31.8 g, 50% yield, 83.6% ee). The solid is redissolved in 240 mL of ethanol at 55°–60° C. and the solution is cooled to room temperature and stirred at room temperature for 2 hours and at 0°–5° C. for 1 hour. The resulting solid is collected by filtration and dried at 40° C. and 28 inches of Hg for 2 hours as (R)-4-benzyl albuterol D-DBTA salt (22.9 g, 37.1% yield, 99.3% ee). The salt (22.9 g) is then treated with 204 mL of 5 wt % aq. Na$_2$CO$_3$ solution in 570 mL of ethyl acetate. The solid is worked-up, and recrystallization from 30 mL of ethyl acetate and 30 mL of n-heptane gives optically pure (R)-4-benzyl albuterol free base (compound IIC) as a white powder (10.1 g, 34.1% yield from racemic Compound IIA, 99.6% ee and 99.8% purity).

EXAMPLE 9

A mixture of (R)-4-benzyl albuterol as a free base (compound IIc) from Example 8 (3.2 g, 9.73 mmol) and 10% Pd/C (0.64 g) in 24 mL of ethanol (denatured with 5 vol % 2-propanol) is shaken on a Parr-hydrogenator under 50 psi of hydrogen at room temperature for 3 hours. The catalyst is removed by filtration and the filtrate is concentrated to ca. 9 mL in volume containing crude (R)-albuterol (compound IIIa) and treated with anhydrous HCl in ether (1.0M, 9.5 mL, 0.98 eq) at 0°–5° C. After 30 min. at room temperature, 9 mL of MTBE is added to the mixture and the resulting mixture is stirred at room temperature for 30 min. and at 0°–5° C. for 2 hours. The white solid (R)-albuterol hydrochloride is collected by filtration and recrystallized from 25 mL of ethanol and 12.5 mL of MTBE to give pure (R)-albuterol hydrochloride (compound IIIb) as a white powder (2.17 g, 80.9% yield, 99.6% purity).

While the invention has been particularly shown and described with reference to preferred embodiments thereof, it will be understood by those skilled in the art that other changes in form and details may be made therein without departing from the spirit and scope of the invention.

What is claimed is:

1. A method for obtaining a single enantiomer of albuterol, comprising:

dissolving a mixture of enantiomers of methyl 5-[2-[(1, 1-dimethylethyl)amino]-1-hydroxyethyl]-2-(phenylmethoxy)benzoate and a chiral acid in methanol, ethanol or a mixture of the two by heating to form a solution, said chiral acid being selected from the group consisting of (−)-di-toluoyl-L-tartaric acid, (+)-di-toluoyl-D-tartaric acid, (−)-di-benzoyl-L-tartaric acid and (+)-di-benzoyl-D-tartaric acid;

allowing said solution to cool, whereby a salt of primarily one enantiomer crystallizes;

separating said salt from said solution;

liberating the enantiomer from said salt by treatment with a base;

reducing said enantiomer;

debenzylating said enantiomer and recovering a single enantiomer of albuterol.

2. A method according to claim 1 wherein said chiral acid is (+)-di-toluoyl-D-tartaric acid and said enantiomer of methyl 5-[2-[(1,1-dimethylethyl)amino]-1-hydroxyethyl]-2-(phenylmethoxy)benzoate is the R enantiomer.

3. A method according to claim 1 wherein said chiral acid is (+)-di-benzoyl-D-tartaric acid and said enantiomer of methyl 5-[2-[(1,1-dimethylethyl)amino]-1-hydroxyethyl]-2-(phenylmethoxy)benzoate is the R enantiomer.

4. A method according to claim 1 wherein said enantiomer is debenzylated by catalytic hydrogenation.

5. The method of claim 1 wherein said enantiomer is reduced with a borane complex.

6. The method of claim 1 further comprising forming a slurry of said salt in methanol, ethanol or a mixture of the two and refluxing said slurry and allowing said slurry to cool, whereby a salt of primarily one enantiomer crystallizes.

7. A method for obtaining a single enantiomer of albuterol, comprising:

dissolving a mixture of enantiomers of α-[[(1,1-dimethylethyl)amino]methyl]-4-(phenylmethoxy)-1,3-benzenedimethanol and a chiral acid in methanol, ethanol or a mixture of the two by heating to form a solution, said chiral acid being selected from the group consisting of (−)-di-toluoyl-L-tartaric acid, (+)-di-toluoyl-D-tartaric acid, (−)-di-benzoyl-L-tartaric acid and (+)-dibenzoyl-D-tartaric acid;

allowing said solution to cool, whereby a salt of primarily one enantiomer crystallizes;

separating said salt from said solution;

liberating said single enantiomer from said salt by treatment with a base;

debenzylating said enantiomer and recovering optically pure albuterol.

8. A method according to claim 7 wherein said chiral acid is (+)-di-toluoyl-D-tartaric acid and said enantiomer of α-[[(1,1-dimethylethyl)amino]methyl]-4-(phenylmethoxy)-1,3-benzenedimethanol is the R enantiomer.

9. A method according to claim 7 wherein said chiral acid is (+)-di-benzoyl-D-tartaric acid and said enantiomer of α-[[(1,1-dimethylethyl)amino]methyl]-4-(phenylmethoxy)-1,3-benzenedimethanol is the R enantiomer.

10. A method according to claim 7 wherein said enantiomer is debenzylated by catalytic hydrogenation.

11. The method of claim 7 further comprising forming a slurry of said salt in methanol, ethanol or a mixture of the two and refluxing said slurry and allowing said slurry to cool, whereby a salt of primarily one enantiomer crystallizes.

12. A method for obtaining a single enantiomer of methyl 5-[2-[(1,1-dimethylethyl)amino]-1-hydroxyethyl]-2-(phenylmethoxy)benzoate comprising:

(a) dissolving a mixture of enantiomers of methyl 5-[2-[(1,1-dimethylethyl)amino]-1-hydroxyethyl]-2-(phenylmethoxy)benzoate and a chiral acid in methanol, ethanol or a mixture of the two by heating to form a solution, said chiral acid being selected from the group consisting of (−)-di-toluoyl-L-tartaric acid, (+)-di-toluoyl-D-tartaric acid, (−)-di-benzoyl-L-tartaric acid and (+)-di-benzoyl-D-tartaric acid by heating to form a solution;

(b) allowing said solution to cool, whereby a salt of primarily one stereoisomer crystallizes;

(c) separating said salt from said solution;

(d) recrystallizing said salt from the alcohol solvent, whereby a diastereomeric salt having greater than 90% ee of an enantiomer of methyl 5-[2-[(1,1-dimethylethyl)amino]-1-hydroxyethyl]-2-(phenylmethoxy)benzoate is obtained;

(e) separating said diastereomeric salt from the alcohol solvent; and (f) liberating said enantiomer of methyl 5-[2-[(1,1-dimethylethyl)amino]-1-hydroxyethyl]-2-(phenylmethoxy)benzoate from said diastereomeric salt by treatment with base.

13. A method according to claim 12 wherein said chiral acid is (+)-di-toluoyl-D-tartaric acid and said enantiomer of methyl 5-[2-[(1,1-dimethylethyl)amino]-1-hydroxyethyl]-2-(phenylmethoxy)benzoate is the R enantiomer.

14. A method according to claim 12 wherein said chiral acid is (+)-di-benzoyl-D-tartaric acid and said enantiomer of methyl 5-[2-[(1,1-dimethylethyl)amino]-1-hydroxyethyl]-2-(phenylmethoxy)benzoate is the R enantiomer.

15. A method for obtaining a single enantiomer of α-[[(1,1-dimethylethyl)amino]methyl]-4-(phenylmethoxy)-1,3-benzenedimethanol comprising:

(a) dissolving a mixture of enantiomers of α-[[(1,1-dimethylethyl)amino]methyl]-4-(phenylmethoxy)-1,3-benzenedimethanol and a chiral acid in methanol, ethanol or a mixture of the two by heating to form a solution, said chiral acid being selected from the group consisting of (−)-di-toluoyl-L-tartaric acid, (+)-di-toluoyl-D-tartaric acid, (−)-di-benzoyl-L-tartaric acid and (+)-di-benzoyl-D-tartaric acid in methanol by heating to form a solution;

(b) allowing said solution to cool, whereby a salt of primarily one stereoisomer crystallized;

(c) separating said salt from said solution;

(d) recrystallizing said salt from the alcohol solvent, whereby a diastereomeric salt having greater than 90% ee of an enantiomer of α-[[(1,1-dimethylethyl)amino]methyl]-4-(phenylmethoxy)-1,3-benzenedimethanol is obtained;

(e) separating said diastereomeric salt from the alcohol solvent; and (f) liberating said enantiomer of α-[[(1,1-dimethylethyl)amino]methyl]-4-(phenylmethoxy)-1,3-benzenedimethanol from said diastereomeric salt by treatment with base.

16. A method according to claim 15 wherein said chiral acid is (+)-di-toluoyl-D-tartaric acid and said enantiomer of α-[[(1,1-dimethylethyl)amino]methyl]-4-(phenylmethoxy)-1,3-benzenedimethanol is the R enantiomer.

17. A method according to claim 15 wherein said chiral acid is (+)-di-benzoyl-D-tartaric acid, said solvent ethanol and said enantiomer of α-[[(1,1-dimethylethyl)amino]methyl]-4-(phenylmethoxy)-1,3-benzenedimethanol is the R enantiomer.

* * * * *